US012662701B2

(12) United States Patent
Chen et al.

(10) Patent No.: US 12,662,701 B2
(45) Date of Patent: Jun. 23, 2026

(54) METHOD FOR SEQUENCING POLYNUCLEOTIDES BASED ON OPTICAL SIGNAL KINETICS OF LUMINESCENT LABELS AND SECONDARY LUMINESCENT SIGNALS

(71) Applicant: Qingdao MGI Tech Co., Ltd., Qingdao (CN)

(72) Inventors: Xi Chen, Shenzhen (CN); Sha Liao, Shenzhen (CN); Wenwei Zhang, Shenzhen (CN); Ao Chen, Shenzhen (CN); Jie Zhao, Shenzhen (CN)

(73) Assignee: QINGDAO MGI TECH C., LTD., Qingdao (CN)

( * ) Notice: Subject to any disclaimer, the term of this patent is extended or adjusted under 35 U.S.C. 154(b) by 1163 days.

(21) Appl. No.: 17/636,746

(22) PCT Filed: Aug. 20, 2019

(86) PCT No.: PCT/CN2019/101530

§ 371 (c)(1),
(2) Date: Feb. 18, 2022

(87) PCT Pub. No.: WO2021/031109

PCT Pub. Date: Feb. 25, 2021

(65) Prior Publication Data

US 2023/0242979 A1 Aug. 3, 2023

(51) Int. Cl.

| | |
|---|---|
| ***C12Q 1/68*** | (2018.01) |
| ***C12Q 1/66*** | (2006.01) |
| ***C12Q 1/6869*** | (2018.01) |
| ***C12Q 1/6876*** | (2018.01) |

(52) U.S. Cl.
CPC ............. *C12Q 1/6869* (2013.01); *C12Q 1/66* (2013.01); *C12Q 1/6876* (2013.01); *C12Q 2600/16* (2013.01)

(58) Field of Classification Search
CPC ...... C12Q 1/6869; C12Q 1/66; C12Q 1/6876; C12Q 2600/16
See application file for complete search history.

(56) References Cited

U.S. PATENT DOCUMENTS

| | | | |
|---|---|---|---|
| 5,302,509 | A | 4/1994 | Cheeseman |
| 9,428,807 | B2 | 8/2016 | Hubbell et al. |
| 9,453,258 | B2 | 9/2016 | Kain et al. |

(Continued)

FOREIGN PATENT DOCUMENTS

| | | | |
|---|---|---|---|
| CN | 1617937 | A | 5/2005 |
| CN | 1940088 | A | 4/2007 |

(Continued)

OTHER PUBLICATIONS

European Application No. 19942121.5, Extended European Search Report mailed on May 10, 2023, 7 pages.

(Continued)

*Primary Examiner* — Jezia Riley
(74) *Attorney, Agent, or Firm* — Kilpatrick Townsend & Stockton LLP

(57) ABSTRACT

Provided are a method for sequencing polynucleotides based on optical signal kinetics of luminescent labels and secondary luminescent signals, in which different luminescence forms and luminescence timings are applied to distinguish the sequential incorporation of different nucleotides, so as to realize the sequencing of the polynucleotides.

13 Claims, 3 Drawing Sheets

Specification includes a Sequence Listing.

(56) References Cited

U.S. PATENT DOCUMENTS

| | | | |
|---|---|---|---|
| 2016/0355541 | A1 | 12/2016 | Jain et al. |
| 2018/0274024 | A1 | 9/2018 | Ju et al. |

FOREIGN PATENT DOCUMENTS

| | | | |
|---|---|---|---|
| CN | 101575639 | A | 11/2009 |
| CN | 102471364 | A | 5/2012 |
| CN | 103087131 | A | 5/2013 |
| CN | 103649335 | A | 3/2014 |
| CN | 103866010 | A | 6/2014 |
| CN | 108864232 | A | 11/2018 |
| CN | 109804087 | A | 5/2019 |
| JP | 2005511058 | A | 4/2005 |
| JP | 2016512206 | A | 4/2016 |
| JP | 2018529632 | A | 10/2018 |
| JP | 2022533916 | A | 7/2022 |
| WO | 2016040607 | A1 | 3/2016 |
| WO | 2018121587 | A1 | 7/2018 |

OTHER PUBLICATIONS

Japanese Application No. 2022-512310, First Office Action mailed on May 18, 2023, 12 pages (6 pages of Original Document and 6 pages of English Translation).

Tan et al., "Design and synthesis of fluorescence-labeled nucleotide with a cleavable azo linker for DNA sequencing", Chemical Communications, Nov. 13, 2015, pp. 954-957, vol. 52, 13.

PCT/CN2019/101530, "International Search Report, translation and Written Opinion", Feb. 25, 2021, 13 pages.

Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis", The Journal of Organic Chemistry, vol. 71, No. 8, Mar. 24, 2006, pp. 3248-3252.

Application No. PCT/CN2019/101530 , International Search Report and Written Opinion, Mailed On Mar. 20, 2020, 16 pages. English Translation of ISR/WO on pp. 1-8.

Tan et al., "Design and Synthesis of Fluorescence-Labeled Nucleotide with a Cleavable Azo Linker for DNA Sequencing", Chemical Communications, vol. 52, No. 5, Nov. 13, 2016.

SEQUENCE LISTING

```
<160> NUMBER OF SEQ ID NOS: 7

<210> SEQ ID NO 1
<211> LENGTH: 233
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gatatctgca ggcatagaat gaatattatt gaatcaataa ttaaagtcgg aggccaagcg     60

gtcttaggaa gacaacaact ccttggctca cagaacgaca tggctacgat ccgactttac    120

tactacgata atgggctgga tacatggaat gattatagat atattaagga ataatgttaa    180

ttaatgccta aattaattaa tctaaggggg ttaatacttc agcctgtgat atc           233


<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

gatatctgca ggcat                                                      15


<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 3

gatatcacag gctga                                                    15


<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

atgcctgcag atatcgatat cacaggctga                                    30


<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

gccatgtcgt tctgtgagcc aagg                                          24


<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

gctcacagaa cgacatggct acgatccgac tt                                 32


<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

tactactacg                                                          10
```

METHOD FOR SEQUENCING POLYNUCLEOTIDES BASED ON OPTICAL SIGNAL KINETICS OF LUMINESCENT LABELS AND SECONDARY LUMINESCENT SIGNALS

CROSS-REFERENCES TO RELATED APPLICATIONS

This application is a national phase application of PCT Application No. PCT/CN2019/101530, filed May 15, 2019, the entire content of which is incorporated herein by reference for all purposes.

REFERENCE TO AN ELECTRONIC SEQUENCE LISTING

The contents of the electronic sequence listing (108518-1303573-5111-US_SL.txt; Size: 2,200 bytes; and Date of Creation: Nov. 20, 2025) is herein incorporated by reference in its entirety.

TECHNICAL FIELD

The present disclosure relates to the field of nucleic acid sequencing. In particular, the present disclosure provides a method for sequencing polynucleotides based on optical signal kinetics of luminescent labels and secondary luminescent signals, in which different luminescence forms and luminescence timings are used to distinguish the sequential incorporation of different nucleotides, so as to realize the sequencing of the polynucleotide.

BACKGROUND

DNA sequencing technology includes the first-generation DNA sequencing technology represented by Sanger sequencing method and the second-generation DNA sequencing technology represented by Illumina Hiseq2500, Roche 454, ABI Solid, BGISEQ-500, etc. In 1977, Sanger invented the dideoxy terminal termination sequencing method which became the representative of the first-generation sequencing technology. In 2001, based on the first-generation sequencing technology, the human genome map was completed. Featured with simple experimental operation, intuitive and accurate results, and short experimental cycle, the Sanger sequencing method has a wide range of applications in such fields having a high requirement for timeliness of detection results as clinical gene mutation detection and genotyping. However, the Sanger sequencing method has the shortcomings of low throughput and high cost, which limits its application in large-scale gene sequencing. In order to overcome the shortcomings of the Sanger sequencing method, the second-generation sequencing technology comes into being. Compared with the first-generation DNA sequencing technology, the second-generation DNA sequencing technology has the characteristics of large sequencing throughput, low cost, high degree of automation, and single-molecule sequencing. Taking the sequencing technology of Hiseq2500V2 as an example, its one experimental process can generate data of 10-200G of bases. The average sequencing cost per base is less than 1/1000 of the sequencing cost of the Sanger sequencing method, and the obtained sequencing results can be processed and analyzed directly by a computer. Therefore, the second-generation DNA sequencing technology is very suitable for large-scale sequencing.

In the past 10 years or so, the second-generation gene sequencing technology has gradually grown from an emerging technology to a mainstream sequencing method, and has gradually become an important testing tool in the clinical field. It is playing a more and more important role in prevention and control of infectious diseases, diagnosis of genetic diseases, non-invasive prenatal screening and other fields. In order to further expand the sequencing market and make sequencers popular, the development of low-cost and miniaturized sequencers has gradually become a development trend in the sequencing field. As classic methods of the second-generation sequencing technology, four-channel, two-channel and single-channel sequencing methods have their own merits. However, through comparison of these three methods, single-channel sequencing has gradually become a development trend in the sequencing field due to its advantages such as less consumables, lower cost, and easier realization of instrument miniaturization and portability. Single-color channel products on the market now mainly include sequencers of ion torrent series, 454 sequencer, and latest Iseq100 launched by Illumina Company.

Single-color signal sequencing is a method where chemiluminescent labels on bases are used to send out the same signal on demand under specific conditions to identify four types of bases to achieve the purpose of sequencing. Featured with simple signal identification, rapid biochemical reaction, and high sequencing throughput, the single-color signal sequencing has become the mainstream method of the second-generation sequencing. Illumina's small rapid sequencers based on monochromatic fluorescence imaging are based on this technology. However, due to the shortcomings of various DNA enrichment methods and the sensitive response of signal response to environmental and instrument conditions, the signal intensity of luminescent labels lacks uniformity in the time dimension and spatial dimension during the test process. In the single-color signal sequencing method, two detections are conducted, the light-emitting state is controlled, and four bases are determined using four light-emitting modes of 1/0, 1/1, 0/1, and 0/0. This detection mode does not distinguish the optical signal by frequency, but only distinguishes it by signal intensity and signal generation time. The excessive dependence of this method on signal intensity leads to the diffusion of sequencing results, which reduces the accuracy of base identification.

Therefore, it is needed in the art for a sequencing method based on single-color signal with higher base identification accuracy.

SUMMARY

In order to solve one of the above-mentioned technical problems, the inventors of the present application have developed a new sequencing method, in which different luminescence forms and luminescence timings are applied to distinguish the four bases of A, (T/U), C, and G. According to the sequencing method of the present disclosure, based on a kinetic curve of chemiluminescence reaction, a chemiluminescent label on a specific base is inactivated by a selective chemical bond breaking method, and the secondary luminescence determination is performed by virtue of the luminescence ability of the remaining luminescent label to identify the base. Since only two characteristics of Flash and Glow are required for the kinetic curve of chemiluminescence, the confusion caused by the unobvious characteristics of the kinetic curve can be greatly reduced. In the meanwhile, for the secondary luminescence, only the signal intensity is required to exceed a background value and the characteristics of the kinetic curve are not required, so the adverse effect of side reactions on signal identification during the reaction process can be reduced, and the accuracy of base identification can be improved.

In one aspect, the present disclosure provides a method for sequencing a nucleic acid molecule, including monitoring sequential incorporation of nucleotides complementary to the nucleic acid molecule, wherein the nucleotides are respectively attached to chemiluminescent labels that induce luminescence having different luminescence kinetics, wherein each incorporated nucleotide is identified by detecting luminescence kinetics of a chemiluminescence reaction in which the chemiluminescent label participates and then removing part of the chemiluminescent labels.

In a specific embodiment, the ribose or deoxyribose moiety of each nucleotide contains a protective group attached via a 2' or 3' oxygen atom, and the protective group is modified or removed after the incorporation of each nucleotide so as to expose a 3'-OH group.

In a specific embodiment, part of the chemiluminescent labels are removed separately, and the other part of the chemiluminescent labels and the protective group are removed under the same condition.

In a specific embodiment, the nucleotides are selected from nucleotides A, G, C and T or U.

In a specific embodiment, the detection of the luminescence kinetics of the chemiluminescence reaction in which the chemiluminescent label participates includes: making the chemiluminescent label to come into contact with a suitable substrate to trigger the chemiluminescence reaction, and detecting luminescence kinetics of light emitted therefrom.

In a specific embodiment, the chemiluminescent label is selected from biochemiluminescent labels that induce different luminescence kinetics and any combination thereof.

In a specific embodiment, the chemiluminescent label is selected from luciferases that induce different luminescence kinetics and any combination thereof.

In a specific embodiment, the chemiluminescent label is a combination of two luciferases that induce different luminescence kinetics.

In a specific embodiment, the light emission is in forms of flash and glow.

In one aspect, the present disclosure provides a method for sequencing a nucleic acid molecule, including:

(1) providing four nucleotides, wherein a first nucleotide is labeled with a first chemiluminescent label through a second linker, a second nucleotide is labeled with the first chemiluminescent label through a first linker, a third nucleotide is labeled with a second chemiluminescent label through a third linker, and a fourth nucleotide is not labeled with any chemiluminescent label;
(2) incorporating one of the four nucleotides into a complementary strand of the nucleic acid molecule;
(3) detecting the chemiluminescent label of the nucleotide in step (2);
(4) adding a cleavage reagent to cleave the second linker;
(5) detecting the chemiluminescent label of the nucleotide after cleavage to determine a type of the nucleotide incorporated;
(6) removing the remaining chemiluminescent label; and optionally repeating steps (2) to (5) or (2) to (6) one or more times in order to determine a sequence of the nucleic acid molecule.

In a specific embodiment, detecting the chemiluminescent label of the nucleotide in steps (2) and (5) includes: making the chemiluminescent label to come into contact with a suitable substrate to trigger the chemiluminescence reaction, and detecting luminescence kinetics of light emitted therefrom.

In a specific embodiment, the chemiluminescent label is selected from biochemiluminescent labels that induce different luminescence kinetics and any combination thereof.

In a specific embodiment, the chemiluminescent label is selected from luciferases that induce different luminescence kinetics and any combination thereof.

In a specific embodiment, the chemiluminescent label is a combination of two luciferases that induce different luminescence kinetics.

In a specific embodiment, the ribose or deoxyribose moiety of each nucleotide contains a protective group attached via a 2' or 3' oxygen atom, and the protective group is modified or removed after the incorporation of the nucleotide so as to expose a 3'-OH group.

In a specific embodiment, part of the chemiluminescent labels are removed separately, and the other part of the chemiluminescent labels and the protective group are removed under the same condition.

In a specific embodiment, the first linker and the third linker are the same or different, and the second linker is different from the third linker.

In a specific embodiment, the nucleotides are selected from nucleotides A, G, C and T or U.

In various aspects, the attachment between the nucleotide and the chemiluminescent label includes attachment mediated by an affinity interaction.

In a specific embodiment, the affinity interaction is selected from antigen-antibody interactions and biotin-avidin (e.g., streptavidin) interactions.

In a specific embodiment, by attaching the chemiluminescent label to one of members participating in the affinity interaction and attaching the nucleotide to the other member participating in the affinity interaction, the chemiluminescent label is attached to the nucleotide through the affinity interaction between the members.

In a specific embodiment, the member attached to the nucleotide is a biotin and the member attached to the chemiluminescent label is an avidin (e.g., streptavidin).

In a specific embodiment, the member attached to the nucleotide is digoxin and the member attached to the chemiluminescent label is an anti-digoxin antibody.

In a specific embodiment, the member attached to the nucleotide is a biotin and the member attached to the chemiluminescent label is an avidin (e.g., streptavidin), wherein digoxin and the avidin are bound by affinity with an anti-digoxin antibody attached to the biotin.

In a specific embodiment, the first nucleotide is attached to a first luciferase through a second linker (linker 2), the second nucleotide is attached to a first luciferase through a first linker (linker 1), the third nucleotide is attached to a second luciferase through a third linker (linker1), and the fourth nucleotide is not attached to any luciferase.

The first linker and the third linker are the same or different, and the second linker and the third linker are different.

In one aspect, the present disclosure provides a method for sequencing a nucleic acid molecule, including the following steps:

(1) providing a to-be-sequenced nucleic acid molecule attached to a support, or attaching a to-be-sequenced nucleic acid molecule to a support;

(2) adding a primer for initiating a nucleotide polymerization reaction, a polymerase for performing a nucleotide polymerization reaction, and four nucleotides, thereby forming a reaction system containing a solution phase and a solid phase, wherein the four nucleotides are derivatives of nucleotides A, (T/U), C, and G respectively, and have the ability of complementary base pairing; and, a hydroxyl group (—OH) at the 3' site of ribose or deoxyribose of each of the four nucleotides is protected by a protective group; and among the four nucleotides, the first nucleotide is attached to a first molecular label through a cleavable linker 2, the second nucleotide is attached to a first molecular label through a cleavable linker 1, the third nucleotide is attached to a second molecular label through a cleavable linker 1, and the fourth nucleotide is not attached to any molecular label;

(3) annealing the primer to the to-be-sequenced nucleic acid molecule, the primer which serves as an initial growing nucleic acid strand and the to-be-sequenced nucleic acid molecule together form a duplex attached to the support;

(4) under conditions that allow the polymerase to perform a nucleotide polymerization reaction, making the polymerase to perform the nucleotide polymerization reaction, thereby incorporating one of the four nucleotides into the 3' end of the growing nucleic acid strand;

(5) making the duplex in the previous step to come into contact with two different luciferases and perform a binding reaction, wherein the two luciferases being capable of specifically binding the first molecular label and the second molecular label respectively, and then making the luciferases to undergo a fluorescence reaction in the presence of substrate(s), and detecting a fluorescence signal emitted;

(6) adding a cleavage solution to cleave the linker 2, and then making the luciferases to undergo the fluorescent reaction in the presence of the substrate(s) again, and detecting a fluorescence signal emitted;

(7) removing the molecular label of each nucleotide; and (8) optionally repeating steps (3) to (7) to obtain sequence information of the nucleic acid molecule.

In a specific embodiment, the first molecular label is a biotin, the first luciferase is attached to a streptavidin, and the nucleotide is attached to the first luciferase through the affinity of the biotin and the streptavidin.

In a specific embodiment, the second molecular label is digoxin, the second luciferase is attached to an anti-digoxin antibody, and the nucleotide is attached to the second luciferase through the affinity of the digoxin and the anti-digoxin antibody.

In the embodiments of the present disclosure, molecular labels are attached to nucleotide derivatives through different linkers, and then luciferases which can specifically bind to the molecular labels are added, and fluorescence signals emitted by the luciferases before and after the cleavage of the linkers are then detected to distinguish the sequential incorporation of different nucleotides, thus realizing the sequencing of a polynucleotide. In a specific embodiment, the first nucleotide is attached to the first molecular label through linker 2, or through linker 1-linker 2; the second nucleotide is attached to the first molecular label through linker1; the third nucleotide is attached to the second molecular label through linker1; the fourth nucleotide is not attached to any molecular label. Luciferases which can specifically bind the first and second molecular labels respectively and the corresponding substrate(s) of the luciferases are added to detect a first luminescent signal; then the linker is broken as needed, and then a second luminescent signal after the break is detected; bases can be identified according to the luminescence of the four nucleotides.

Therefore, in an exemplary embodiment, the method for sequencing a nucleic acid molecule in the present disclosure includes the following steps:

(1) providing a to-be-sequenced nucleic acid molecule attached to a support, or attaching a to-be-sequenced nucleic acid molecule to a support;

(2) adding a primer for initiating a nucleotide polymerization reaction, a polymerase for performing a nucleotide polymerization reaction, and four nucleotides, thereby forming a reaction system containing a solution phase and a solid phase, wherein the four nucleotides are derivatives of nucleotides A, (T/U), C, and G respectively, and have the ability of complementary base pairing; and, a hydroxyl group (—OH) at the 3' site of ribose or deoxyribose of each of the four nucleotides is protected by a protective group; and among the four nucleotides, the first nucleotide is attached to a first molecular label through a cleavable linker 2, the second nucleotide is attached to a first molecular label through a cleavable linker 1, the third nucleotide is attached to a second molecular label through a cleavable linker 1, and the fourth nucleotide is not attached to any molecular label;

(3) annealing the primer to the to-be-sequenced nucleic acid molecule, the primer which serves as an initial growing nucleic acid strand and the to-be-sequenced nucleic acid molecule together form a duplex attached to the support;

(4) under conditions that allow the polymerase to perform a nucleotide polymerization reaction, making the polymerase to perform the nucleotide polymerization reaction, thereby incorporating one of the four nucleotides into the 3' end of the growing nucleic acid strand;

(5) removing the solution phase of the reaction system of the previous step, remaining the duplex attached to the support; and adding two different luciferases to carry out a binding reaction, the two luciferases being capable of specifically binding the first molecular label and the second molecular label respectively;

(6) removing unbound luciferase with an elution buffer;

(7) adding substrate(s) of the luciferases and detecting a curve of fluorescence signal over time;

(8) removing the solution of the previous reaction step;

(9) adding a cleavage solution to cleave the linker 2;

(10) adding substrate(s) of the luciferases and detecting a curve of fluorescence signal over time;

(11) optionally removing the linker 1 and 3' protective group of each nucleotide;

(12) optionally removing the solution of the previous reaction step; and

(13) optionally repeating steps (3) to (12) or steps (3) to (10) one or more times to obtain sequence information of the nucleic acid molecule.

In a specific embodiment, the first molecular label is a biotin, the first luciferase is attached to a streptavidin, and the nucleotide is attached to the first luciferase through the affinity of the biotin and the streptavidin.

In a specific embodiment, the second molecular label is digoxin, the second luciferase is attached to an anti-digoxin antibody, and the nucleotide is attached to the second luciferase through the affinity of the digoxin and the anti-digoxin antibody.

In a specific embodiment, the attachment of the two luciferases to the nucleotides can also be carried out separately. For example, the first luciferase labeled with the first label can be added first to have a binding reaction with the nucleotide labeled with the first molecular label, the unbound first luciferase is then washed out with an elution buffer, and then the substrate of the first luciferase is added and a fluorescence signal is detected; next, the second luciferase labeled with the second label can be added to have a binding reaction with the nucleotide labeled with the second molecular label, the unbound second luciferase is then washed out with an elution buffer, and then the substrate of the second luciferase is added, and a fluorescence signal is detected. Specifically, the present disclosure provides a method for sequencing a nucleic acid molecule, including the following steps:

(1) providing a to-be-sequenced nucleic acid molecule attached to a support, or attaching a to-be-sequenced nucleic acid molecule to a support;
(2) adding a primer for initiating a nucleotide polymerization reaction, a polymerase for performing a nucleotide polymerization reaction, and four nucleotides, thereby forming a reaction system containing a solution phase and a solid phase, wherein the four nucleotides are derivatives of nucleotides A, (T/U), C, and G respectively and have an ability of complementary base pairing; and, a hydroxyl group (—OH) at the 3' site of ribose or deoxyribose of each of the four nucleotides is protected by a protective group; and among the four nucleotides,
  the first nucleotide is attached to a first molecular label through a cleavable linker 2,
  the second nucleotide is attached to a first molecular label through a cleavable linker 1,
  the third nucleotide is attached to a second molecular label through a cleavable linker 1, and
  the fourth nucleotide is not attached to any molecular label;
(3) annealing the primer to the to-be-sequenced nucleic acid molecule, the primer which serves as an initial growing nucleic acid strand and the to-be-sequenced nucleic acid molecule together form a duplex attached to the support;
(4) under conditions that allow the polymerase to perform a nucleotide polymerization reaction, making the polymerase to perform the nucleotide polymerization reaction, thereby incorporating one of the four nucleotides into the 3' end of the growing nucleic acid strand;
(5) removing the solution phase of the reaction system of the previous step, remaining the duplex attached to the support; and adding a first luciferase to carry out a binding reaction, the first luciferase being capable of specifically binding the first molecular label;
(6) removing unbound first luciferase with an elution buffer;
(7) adding a substrate of the first luciferase and detecting a curve of fluorescence signal over time;
(8) removing the solution of the previous reaction step;
(9) adding a second luciferase to carry out a binding reaction, the second luciferase being capable of specifically binding the second molecular label;
(10) removing unbound second luciferase with an elution buffer;
(11) adding a substrate of the second luciferase and detecting a curve of fluorescence signal over time;
(12) optionally removing the solution of the previous reaction step;
(13) adding a cleavage solution to cleave the linker 2;
(14) adding a substrate of a luciferase and detecting a curve of fluorescence signal over time;
(15) optionally removing the linker 1 and 3' protective group of each nucleotide;
(16) optionally removing the solution of the previous reaction step; and
(17) optionally repeating steps (3) to (16) or steps (3) to (14) one or more times to obtain sequence information of the nucleic acid molecule.

In another aspect, the present disclosure further relates to a kit for sequencing a polynucleotide, including:

(a) four nucleotides, wherein the four nucleotides are derivatives of nucleotides A, (T/U), C, and G respectively and have an ability of complementary base pairing; and, a hydroxyl group (—OH) at the 3' site of ribose or deoxyribose of each of the four nucleotides is protected by a protective group; and among the four nucleotides,
  the first nucleotide is attached to a first molecular label through a cleavable linker 2,
  the second nucleotide is attached to a first molecular label through a cleavable linker 1,
  the third nucleotide is attached to a second molecular label through a cleavable linker 1, and
  the fourth nucleotide is not attached to any molecular label;
b) two luciferases, wherein the two luciferases can specifically bind the first molecular label and the second molecular label, respectively, and the two luciferases are different mutants of the same luciferase or are different luciferases; and
(c) a cleavage solution for cleaving the linker 2.

In some preferred embodiments, the kit of the present disclosure further includes: a reagent and/or a device for extracting a nucleic acid molecule from a sample; a reagent for pretreating the nucleic acid molecule; a support to be attached to a to-be-sequenced nucleic acid molecule; a reagent for attaching the to-be-sequenced nucleic acid molecule to the support in, for example, a covalent or non-covalent way; a primer for initiating a nucleotide polymerization reaction; a polymerase for carrying out the nucleotide polymerization reaction; one or more buffer solutions; one or more washing solutions; or any combination thereof.

DETAILED SUMMARY

Figure 1:
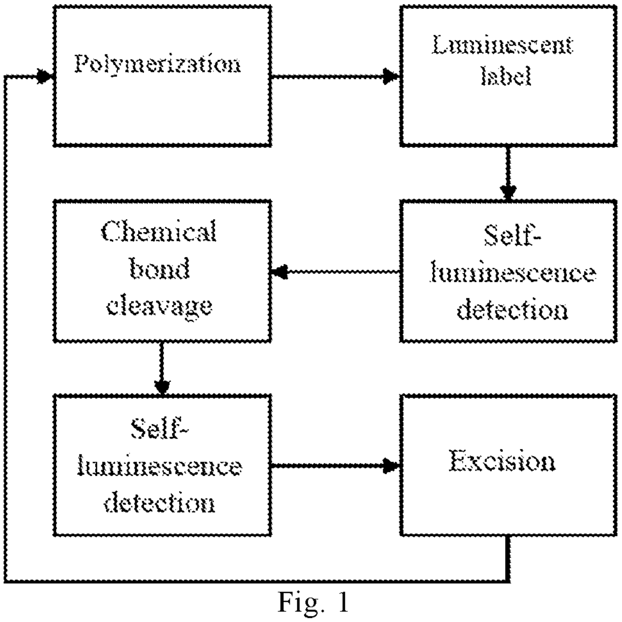
FIG. 1 shows a flow chart of a sequencing method according to the present disclosure.

Unless otherwise defined, all technical and scientific terms used herein have the same meanings as commonly understood by one of ordinary skill in the art to which the present disclosure pertains. All patents, applications and other publications mentioned herein are incorporated by reference in their entirety. If the definitions set forth herein conflict or are inconsistent with the definitions described in patents, applications, and other publications incorporated herein by reference, the definitions described herein shall prevail.

As used herein, the term "polynucleotide" refers to deoxyribonucleic acid (DNA), ribonucleic acid (RNA), or analogs thereof. The polynucleotide can be single-stranded, double-stranded, or contain both single-stranded and double-stranded sequences. A polynucleotide molecule can be derived from a double-stranded DNA (dsDNA) form (e.g., genomic DNA, PCR and amplification products, etc.), or can be derived from a single-stranded DNA (ssDNA) or RNA form and can be converted into dsDNA form, and vice versa. The exact sequence of the polynucleotide molecule is known or unknown. The following are exemplary examples of the polynucleotides: genes or gene fragments (e.g., probes, primers, EST or SAGE tags), genomic DNA, genomic DNA fragments, exons, introns, messenger RNA (mRNA), transport RNA, ribosomal RNA, ribozyme, cDNA, recombinant polynucleotides, synthetic polynucleotides, branched polynucleotides, plasmids, supports, isolated DNA of any sequence, isolated RNA of any sequence, and nucleic acid probes, primers or amplified copies of any of the above sequences.

The polynucleotides may include nucleotides or nucleotide analogs. A nucleotide usually contains a sugar (such as ribose or deoxyribose), a base, and at least one phosphate group. The nucleotide can be base-free (i.e. lacking base). The nucleotides include deoxyribonucleotides, modified deoxyribonucleotides, ribonucleotides, modified ribonucleotides, peptide nucleotides, modified peptide nucleotides, modified phosphate-sugar backbone nucleotides and mixtures thereof. Examples of the nucleotides include, for example, adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP) and deoxyuridine triphosphate (dUTP). Nucleotide analogs containing modified bases can also be used in the methods described herein. With a natural backbone or a similar structure, exemplary modified bases that can be included in the polynucleotide include, for example, inosine, xathanine, hypoxathanine, isocytosine, isoguanine, 2-aminopurine, 5-methylcytosine, 5-hydroxymethylcytosine, 2-aminoadenine, 6-methyladenine, 6-methylguanine, 2-propylguanine, 2-propyladenine, 2-thiouracil, 2-thiothymine, 2-thiocytosine, 15-halogenated uracil, 15-halogenated cytosine, 5-propynyluracil, 5-propynylcytosine, 6-azouracil, 6-azocytosine, 6-azothymine, 5-uracil, 4-thiouracil, 8-halogenated adenine or guanine, 8-aminoadenine or guanine, 8-thioadenine or guanine, 8-thioalkyl adenine or guanine, 8-hydroxyadenine or guanine, 5-halogen substituted uracil or cytosine, 7-methylguanine, 7-methyladenine, 8-azaguanine, 8-azaadenine, 7-deazaguanine, 7-deazaadenine, 3-deazaguanine, 3-deazaadenine, and more. As known in the art, certain nucleotide analogs cannot be incorporated into polynucleotides. For example, the nucleotide analog is adenosine 5'-phosphoryl sulfate.

Generally speaking, the nucleotide refers to nucleotide A, C, G, T or U. As used herein, the term "nucleotide A" refers to a nucleotide containing adenine (A) or its modified derivative or analog, such as ATP and dATP. "Nucleotide G" refers to a nucleotide containing guanine (G) or its modified derivative or analog, such as GTP and dGTP. "Nucleotide C" refers to a nucleotide containing cytosine (C) or its modified derivative or analog, such as CTP and dCTP. "Nucleotide T" refers to a nucleotide containing thymine (T) or its modified derivative or analog, such as TTP and dTTP. "Nucleotide U" refers to a nucleotide containing uracil (U) or its modified derivative or analog, such as UTP and dUTP.

Nucleotide Labeling

The present disclosure relates to using different labels to label nucleotides by virtue of different linkers, thereby attaching different luciferases to the nucleotides.

As used herein, the term "chemiluminescent label" refers to any compound that can be attached to a nucleotide and it can trigger a chemiluminescence reaction by contact with a suitable substrate, thereby generating a detectable optical signal without the need for excitation light. Generally speaking, any component participating in the chemiluminescence reaction can be used as the chemiluminescent label as described herein. Correspondingly, other components participating in the chemiluminescence reaction are referred to herein as the substrate of the chemiluminescent label. Examples of commonly used suitable chemiluminescent labels include, but are not limited to, peroxidase, alkaline phosphatase, luciferase, aequorin, functionalized iron-porphyrin derivatives, luminal, luminol, isoluminol, acridine ester, sulfonamide, and more. The substrate of the chemiluminescent label will depend on the specific chemiluminescent label used. For example, the substrate of alkaline phosphatase can be AMPPD (adamantyl 1,2-dioxane aromatic phosphate), the substrate of luciferase can be luciferin, and the substrate of acridinium ester can be a mixture of sodium hydroxide and $H_2O_2$ and more. For a detailed description of chemiluminescent labels and their corresponding substrates, see, for example, Larry J. Kricka, Chemiluminescent and Bioluminescent Techniques, CLIN. CHEM. 37/9, 1472-1481 (1991) and Tsuji, A. et al. (2005) Bioluminescence and chemiluminescence: Progress and perspectives. World Scientific: [sl]. ISBN 978-981-256-118-3. 596 pp.

In a preferred embodiment, the chemiluminescent labels as used herein are biochemiluminescent labels.

As used herein, the term "biochemiluminescent label" refers to any compound that can be attached to a nucleotide and it can trigger a bioluminescence reaction by contact with a suitable substrate, thereby generating a detectable optical signal without the need for excitation light. Bioluminescence is a type of chemiluminescence and it refers to emission of light during a chemical reaction that occurs in the body or in the secretions of certain types of organisms. Examples of biochemiluminescent labels may include, for example, luciferase, aequorin, glucose dehydrogenase, glucose oxidase, and more. The substrate of the biochemiluminescent label will depend on the specific biochemiluminescent label used. For example, the substrate of luciferase may be luciferin, and the substrate of aequorin may be calcium ion. For a detailed description of chemiluminescent labels and their corresponding substrates, see, for example, Larry J. Kricka, Chemiluminescent and Bioluminescent Techniques, CLIN. CHEM. 37/9, 1472-1481 (1991) and Tsuji, A. et al. (2005) Bioluminescence and chemiluminescence: Progress and perspectives. World Scientific: [sl]. ISBN 978-981-256-118-3. 596 pp.

In a preferred embodiment, the biochemiluminescent label as used herein is luciferase. In a specific embodiment, the luciferase is selected from gaussia luciferase, renilla luciferase, dinoflagellate luciferase, firefly luciferase, fungal luciferase, bacterial luciferase and vargula luciferase.

As used herein, "labeling a nucleotide with a chemiluminescent label" means attaching a chemiluminescent label to a nucleotide. The specific manner of attaching the chemiluminescent label to the nucleotide is known to those skilled in the art. For example, reference can be made to the related description in the following documents (all incorporated herein by reference): Sambrook et al., Molecular Cloning, A Laboratory Manual, 2nd Edition (Cold Spring Harbor Laboratory Press, Cold Spring Harbor, NY, 1989), Chapter 10; U.S. Pat. Nos. 4,581,333, 5,283,174, 5,547,842, 5,656,207 and 5,658,737. In one embodiment, the chemiluminescent label can be directly attached to the nucleotide via a covalent bond. In another embodiment, the chemiluminescent label can be attached to the nucleotide via a linker.

As used herein, the molecular label for labeling the nucleotide and the label on the luciferase can be any pair of molecules that can specifically bind to each other. The specific binding between the paired members realizes the attachment of the nucleotide to the luciferase. Exemplary pairing members include but are not limited to: (a) haptenic or antigenic compounds combined with corresponding antibodies or binding parts or fragments thereof, such as digoxin-digoxin antibody, N3G-N3G antibody, FITC-FITC antibody; (b) nucleic acid aptamers and proteins; (c) non-immune binding pairs (such as biotin-avidin, biotin-streptavidin, and biotin-neutravidin); (d) hormone-hormone binding protein; (e) receptor-receptor agonist or antagonist; (f) lectin-carbohydrate; (g) enzyme-enzyme cofactor; (h) enzyme-enzyme inhibitor; and (i) pairs of complementary oligonucleotides or polynucleotides capable of forming a nucleic acid duplex.

In a specific embodiment, the first molecular label and the second molecular label are small molecular labels and selected from biotin, digoxin, N3G and FITC. The two luciferases can specifically bind the first molecular label and the second molecular label, respectively. For example, in a specific embodiment, if the first molecular label is biotin, then the first luciferase can be streptavidin-labeled luciferase; if the second molecular label is digoxin, then the second luciferase can be a luciferase that is labeled with a digoxin antibody and is different from the first luciferase, and the second luciferase can also be different mutants of a luciferase as same as the first luciferase and labeled with a digoxin antibody. The different luciferases can correspond to the same substrate or different substrates as long as the luminescence forms of the two enzymes reacting with the substrate are different; different mutants of the same luciferase can also correspond to the same substrate or different substrates as long as the luminescence forms of the different mutants reacting with the substrate are different, and it is preferred that different mutants of the same luciferase correspond to the same substrate. The source of the luciferase includes, but is not limited to, firefly, gaussia, renilla, oplophorus and other organisms. For example, the streptavidin-labeled luciferase can be SA-Gluc: Streptavidin-*Gaussia princeps* luciferase from Adivity Company; or nanoKAZ from Promega Company; or nanoLuc from Nanolight Company; or a corresponding Glow morphological mutant or Flash morphological mutant. The luciferase labeled with digoxin antibody can be digoxin antibody-Gluc or digoxin antibody-Nluc or digoxin antibody-nanoKAZ, and the corresponding Glow morphological mutant or Flash morphological mutant. Its corresponding substrate can be coelenterazine, dehydroxylated coelenterazine, fluorine-substituted coelenterazine, furan ring-substituted coelenterazine, or other similar modified coelenterazines.

In an embodiment of the present disclosure, the first molecular label and the second molecular label are attached to the nucleotide derivatives through cleavable linkers. The linkers are guaranteed to be broken on demand during the reaction. For example, in a specific embodiment, the first nucleotide is attached to the first molecular label through the cleavable linker 2, or the first nucleotide is attached to the first molecular label through the cleavable linker 1-linker 2; the second nucleotide is attached to the first molecular label through the cleavable linker 1; the third nucleotide is attached to the second molecular label through the cleavable linker 1; the fourth nucleotide is not attached to any molecular label. The linkers described therein include but are not limited to disulfide bonds, azides, linkers containing cis-aconitic anhydride, and more.

Sequencing of Polynucleotide

Preferably, the nucleotides of the present disclosure attached to different luciferases are suitable for sequencing by synthesis. Methods for sequencing by synthesis as used herein are various well-known methods for sequencing by synthesis in the art. Basically, in sequencing by synthesis, a to-be-sequenced nucleic acid molecule is first hybridized with a sequencing primer, and then in the presence of a polymerase, with the to-be-sequenced nucleic acid molecule as a template, the nucleotides linked with different luciferases as described herein are polymerized at the 3' end of the sequencing primer. After polymerization, the nucleotides are identified by detecting the fluorescence signals emitted by the luciferases. After the luciferases are removed from the labeled nucleotides, the next polymerization sequencing cycle is performed.

A method for sequencing a target polynucleotide can be carried out as follows: denaturing the sequence of the target polynucleotide so that the target polynucleotide comes into contact with different nucleotides, respectively, so as to form a complement of the target polynucleotide, and then detecting the incorporation of said nucleotides. The method adopts polymerization so that the nucleotide which is complementary to the target polynucleotide is incorporated by virtue of a polymerase, thereby extending the complementary strand. The polymerization reaction also requires a special primer to initiate the polymerization.

For each round of reaction, the incorporation of the nucleotide is carried out by a polymerase, and then the incorporation event is measured. There are many different polymerases, and it is easy for a person of ordinary skill in the art to determine the most suitable polymerase. Preferably, the enzymes include DNA polymerase I, Klenow fragment, DNA polymerase III, T4 or T7 DNA polymerase, Taq polymerase or vent polymerase. Polymerases engineered to have specific properties may also be used.

The sequencing method is preferably performed on the target polynucleotide arranged on a solid support. A plurality of target polynucleotides can be immobilized on the solid support through adaptor molecules, or can be attached to particles such as microspheres, and the particles can be attached to a solid support material.

The polynucleotide can be attached to the solid support in many ways, including use of biotin-streptavidin interaction. Methods for immobilizing polynucleotides on a solid support are well known in the art and include lithography techniques and spotting each polynucleotide on a specific position on the solid support. Suitable solid supports are well known in the art and include glass slides and beads, ceramic and silicon surfaces, and plastic materials. The support is usually flat. Microbeads (microspheres) may also be used, and can be attached to other solid supports by known methods. The microspheres can have any suitable size, and their diameters are usually 10 to 100 nanometers. In a preferred embodiment, the polynucleotide is directly attached to a flat surface, preferably to a flat glass surface. The attachment is preferably carried out in the form of a covalent bond. The array used is preferably a single molecule array, which includes a polynucleotide located in a unique optically resolvable region, for example the one as described in International Application No. WO00/06770.

The necessary conditions for polymerization are well known to those skilled in the art. In order to perform the polymerase reaction, usually a primer sequence must first be annealed to the target polynucleotide. The primer sequence is identified by the polymerase and serves as a starting site for the subsequent extension of the complementary strand. The primer sequence can be added as an independent component relative to the target polynucleotide. In addition, the primer and the target polynucleotide may each be a part of a single-stranded molecule, and an intramolecular duplex, that is, a hairpin loop structure, is formed by the primer part and a part of the target. The structure can be immobilized on the solid support at any site of the molecule. Other conditions necessary for carrying out the polymerase reaction are well known to those skilled in the art, and these conditions include temperature, pH, and buffer composition.

Subsequently, the labeled nucleotides of the present disclosure come into contact with the target polynucleotide to carry out polymerization. The nucleotides can be added sequentially, that is, each type of nucleotide (A, C, G or T/U) is added separately, or they can be added at the same time.

The polymerization was carried out for a period that is long enough to incorporate one nucleotide.

Then, the unincorporated nucleotides are removed, for example, by removing the solution phase from the reaction system in the previous step and maintaining the duplexes attached to the support.

Subsequently, two luciferases containing different luciferases can be added to carry out binding reactions. The two luciferases can respectively specifically bind the molecular labels for labeling nucleotides, thereby achieves the attachment of luciferases to the incorporated nucleotides. Then, the corresponding substrate(s) of the luciferases are added and the fluorescence signals are detected. Two luciferases containing different mutants of the same luciferase may also be added to carry out binding reactions. The luciferases can respectively specifically bind the molecular labels for labeling nucleotides, thereby attaching the luciferases to the incorporated nucleotides. Then, the corresponding substrate (s) of the luciferases are added and the fluorescence signals are detected.

Then, a cleavage solution is added for cleaving the linker 2 so that the molecular label attached to the nucleotide through linker 2 is removed; the cleavage solution is then removed by using an elution buffer; the substrate of the luciferase is added again, and the second luminescent signal is detected by a microplate reader to determine a base sequence.

In a specific embodiment, the four deoxyribonucleotide analogs are labeled with different small molecule labels biotin (abbreviated as B) and digoxin (abbreviated as D). For example, nucleotide A is labeled with B by linker 1-linker 2, nucleotide C is labeled with B by linker 1, nucleotide T is labeled with D by linker 1, and nucleotide G is not labeled. The 3' end hydroxyl groups of the four deoxyribonucleotide analogs labeled with different small molecules are all blocked to ensure that only one deoxyribonucleotide is bound in each sequencing reaction. During the sequencing reaction process, the four deoxynucleotide analogues and the sequencing polymerase mixture are first introduced. Under the action of the polymerase, a deoxyribonucleotide analog is incorporated into the 3' end of the growing nucleic acid strand according to the principle of complementary base pairing. Unbound deoxyribonucleotide analogs can be removed by removing the solution phase from the reaction system in the previous step and maintaining the duplexes attached to the support. Then, two luciferases containing different luciferases are added. The first luciferase is labeled with streptavidin and binds nucleotide A or nucleotide C labeled with small molecule B. The second luciferase is labeled with a digoxin antibody and binds the nucleotide T labeled with a small molecule D. After the unbound luciferase is removed with the elution solution, the substrate(s) of the luciferases is added, and signal detection is performed by a detector, thereby obtaining a first fluorescence signal. Then, a cleavage solution capable of selectively cleaving the linker 2 is added. Linker 2 is cleaved but linker 1 is not cleaved. The substrate(s) of the luciferases is added again, and signal detection is performed by a detector, thereby obtaining a second fluorescence signal. According to the two reaction signals, base identification can be carried out.

In a specific embodiment, the attachment of two luciferases containing different luciferases or two luciferases containing different mutants of the same luciferase to deoxynucleotide analogs and signal detection can be performed separately. First, the first luciferase labeled with streptavidin is added and binds nucleotide A or nucleotide C labeled with small molecule B. After the unbound first luciferase is removed with an elution solution, the substrate of the first luciferase is added, the nucleotide attached to the first luciferase emit light, and then signal detection is performed by a detector. After the reaction solution is removed, a second luciferase labeled with digoxin antibody is added and binds the nucleotide T labeled with a small molecule D; then, the unbound second luciferase is removed with the elution solution; the substrate of the second luciferase is added, the base attached to the second luciferase emits light, and then signal detection is performed by the detector, thereby obtaining a first fluorescence signal. Then, a cleavage solution capable of selectively cleaving the linker 2 is added. Linker 2 is cleaved but linker 1 is not cleaved. The substrate of the first luciferase is added again, the nucleotide attached to the first luciferase emits light, and then signal detection is performed by the detector. The substrate of the second luciferase is added and the nucleoside attached to the second luciferase emits light, and then signal detection is performed by the detector, thereby obtaining a second fluorescence signal. According to the two reaction signals, base identification can be carried out.

In another specific embodiment, the four deoxyribonucleotide analogs are labeled with different small molecule labels biotin (abbreviated as B) and digoxin (abbreviated as D). For example, nucleotide A is labeled with B by linker 1-linker 2, nucleotide C is labeled with B by linker1, nucleotide T is labeled with D by linker 1, and nucleotide G is not labeled. The 3' end hydroxyl groups of the four deoxyribonucleotide analogs labeled with different small molecules are all blocked to ensure that only one deoxyribonucleotide is bound in each sequencing reaction. During the sequencing reaction process, the four deoxynucleotide analogues and the sequencing polymerase mixture are first introduced. Under the action of the polymerase, a deoxyribonucleotide analog is incorporated into the 3' end of the growing nucleic acid strand according to the principle of complementary base pairing. Unbound deoxyribonucleotide analogs can be removed by removing the solution phase from the reaction system in the previous step and maintaining the duplexes attached to the support. Then, two luciferases containing different mutants of the same luciferase are added. The first luciferase is labeled with streptavidin and binds nucleotide A or nucleotide C labeled with small molecule B. The second luciferase is labeled with a digoxin antibody and binds the nucleotide T labeled with a small molecule D. After the unbound luciferase is removed with the elution solution, the substrate(s) of the luciferases is added, and signal detection is performed by a detector, thereby obtaining a first fluorescence signal. Then, a cleavage solution capable of selectively cleaving the linker 2 is added. Linker 2 is cleaved but linker 1 is not cleaved. The substrate(s) of the luciferases is added again, and signal detection is performed by a detector, thereby obtaining a second fluorescence signal. According to the two reaction signals, base identification can be carried out.

Fluorescence Signal Detection

The method for detecting the fluorescence signal is well known in the art. For example, it can be implemented by a device for detecting the wavelength of fluorescence. Such devices are well known in the art. For example, the device may be a confocal scanning microscope that scans the surface of a solid support with a laser in order to image a fluorophore directly bound to the to-be-sequenced nucleic acid molecule. In addition, a sensitive 2-D detector, such as a charge-coupled detector (CCD), can be used to observe each signal generated, for example. Other techniques such as Scanning Near Field Optical Microscopy (SNOM) can also be used, for example.

Removal of Labels

After detection, suitable conditions can be used to remove the labels on the nucleotides.

In a specific embodiment, the nucleotide analog of the present disclosure also has a 3' protective group. In some embodiments of the present disclosure, the protective group and the label are usually two different groups on the 3'-blocked labeled nucleotide. In other embodiments, the protective group and the label may also be the same group.

As used herein, the term "protective group" means a group that prevents a polymerase (which catalyzes the incorporation of a nucleotide containing the group into a polynucleotide strand being synthesized) from further catalyzing the incorporation of another nucleotide after incorporating the nucleotide containing the group into the polynucleotide strand being synthesized. Such protective groups are also referred to herein as 3'-OH protective groups. Nucleotides containing such protective groups are also referred to herein as 3' blocked nucleotides. The protective group can be any suitable group that can be added to the nucleotide, as long as the protective group can prevent additional nucleotide molecules from being added to the polynucleotide strand and can be easily removed from the sugar portion of the nucleotide without damaging the polynucleotide strand. In addition, nucleotides modified with protective groups need to be resistant to polymerases or other suitable enzymes for incorporating the modified nucleotides into the polynucleotide strand. Therefore, an ideal protective group exhibits long-term stability, can be efficiently incorporated by catalysis of polymerase to prevent secondary or further incorporation of nucleotides, and can be preferably removed under a mild condition without damaging the structure of the polynucleotide, preferably under an aqueous condition.

Various protective groups that meet the above description have been described in the prior art. For example, as described in WO 91/06678, 3'-OH protective groups include esters and ethers, —F, —$NH_2$, —$OCH_3$, —$N_3$, —$OPO_3$, —$NHCOCH_3$, 2-nitrobenzene carbonate, 2,4-sulfenyl dinitro and tetrahydrofuran ether. Metzker et al. (Nucleic Acids Research, 22 (20): 4259-4267, 1994) discloses the synthesis and application of eight 3'-modified 2-deoxyribonucleoside 5'-triphosphates (3'-modified dNTPs). WO2002/029003 describes the use of an allyl protective group to cap a 3'-OH group on a growing DNA strand in a polymerase reaction. Preferably, various protective groups reported in International Application Publications WO2014139596 and WO2004/018497 can be used, including, for example, those protective groups illustrated in FIG. 1A and those 3'-OH protective groups (i.e., protective groups) defined in the claims in WO2014139596, and, for example, those protective groups illustrated in FIGS. 3 and 4 and those defined in the claims in WO2004/018497. The above references are all incorporated herein by reference in their entirety.

Those skilled in the art will understand how to attach a suitable protective group to a ribose ring in order to block the interaction with 3'-OH. The protective group can be directly attached to the 3' site, or can be attached to the 2' site (the protective group has sufficient size or charge to block the interaction at the 3' site). In addition, the protective group can be attached to the 3' and 2' sites, and can be cleaved to expose the 3'-OH group.

After successfully incorporating the 3'-blocked nucleotide into the growing nucleic acid strand, the protective group needs to be removed to create a usable 3'-OH site for continuous strand synthesis. The reagents that can remove protective groups from modified nucleotides as used herein depend to a large extent on the protective groups used. For example, removal of a protective ester group from the 3'-OH functional group is usually achieved by alkaline hydrolysis. The ease of removing a protective group varies greatly; generally, the greater the electronegativity of a substituent on the carbonyl carbon, the easier the protective group can be removed. For example, a highly electronegative trifluoroacetic acid group can be rapidly cleaved from the 3'-OH at pH 7 in methanol (Cramer et al., 1963), so the trifluoroacetic acid group is unstable during polymerization at this pH. A phenoxyacetate group is cleaved in less than 1 minute, but at a significantly higher pH, for example, in NH-/methanol (Reese and Steward, 1968). Various hydroxy protective groups can be selectively cleaved using chemical methods other than alkaline hydrolysis. A 2,4-dinitrophenylthio group can be quickly cleaved by treatment with nucleophiles such as thiophenol and thiosulfate (Letsinger et al., 1964). Allyl ether is cleaved by treatment with Hg(II) in acetone/water (Gigg and Warren, 1968). Tetrahydrothiapyranyl ether is removed by use of Ag(I) or Hg(II) under neutral conditions (Cohen and Steele, 1966; Cruse et al., 1978). Photochemical deblocking can be used together with photochemically cleavable protective groups. There are several protective groups that can be used in this method. The use of o-nitrobenzyl ether as a 2'-hydroxyl functional protective group of ribonucleosides is known and proven (Ohtsuka et al., 1978), and the protective group is removed by irradiation at 260 nm. The protective group, alkyl carbonate o-nitrobenzyl carbonate, is also removed by irradiation at pH 7 (Cama and Christensen, 1978). Enzymolysis deblocking of the 3'-OH protective group is also possible. It has been evidenced that T4 polynucleotide kinase can convert a 3'-phosphate end into a 3'-OH end, and then it can be used as a primer for DNA polymerase I (Henner et al., 1983). The 3' protective groups of those dNTP analogs containing phosphate as the protective group can be removed by virtue of the activity of 3'-phosphatase.

Other reagents that can remove protective groups from 3'-blocked nucleotides include, for example, phosphines (e.g., tris(hydroxymethyl)phosphine (THP)), which can, for example, remove the azide-containing 3'-OH protective group from the nucleotide (for this application of phosphine, reference can be made, for example, to the description in WO2014139596, the entire content of which is incorporated herein by reference). Other reagents that can remove protective groups from 3'-blocked nucleotides also include, for example, corresponding reagents for removing 3'-allyl, 3,4-dimethoxybenzyloxymethyl or fluoromethoxymethyl serving as a 3'-OH protective group, as disclosed in the description of WO2004/018497, pages 114 to 116.

In the embodiments of the present disclosure, the nucleotide label is preferably removed together with the protective group after detection.

In some embodiments, the label may be incorporated with a protective group, thereby allowing the label to be removed together with the protective group after the 3'-blocked nucleotide is incorporated into the nucleic acid strand.

In other embodiments, the label may be attached to the nucleotide separately from a protective group by using a linker. Such a label may, for example, be attached to the purine or pyrimidine base of the nucleotide. In some embodiments, the linker used is cleavable. The use of a cleavable linker ensures that the label can be removed after detection, which avoids any signal interference with any labeled nucleotides subsequently incorporated. In other embodiments, a non-cleavable linker can be used. Since subsequent nucleotide incorporation is not required after the labeled nucleotide is incorporated into the nucleic acid strand, the label does not need to be removed from the nucleotide.

In other embodiments, the label and/or linker may have a size or structure sufficient to block the incorporation of other nucleotides into the polynucleotide strand (that is, the label itself can serve as a protective group). The blocking may be caused by steric hindrance, or by a combination of size, charge, and structure.

The cleavable linkers are well known in the art, and conventional chemical methods can be used to attach the linker to the nucleotide base and the label. The linker can be attached to any position of the nucleotide base, provided that Watson-Crick base pairing can still be performed. For purine bases, it is preferred that the attachment of the linker is implemented by position 7 of the purine or preferably, a deaza purine analog, or by 8-modified purine, or by N-6 modified adenine or by N-2 modified guanine. For pyrimidines, the attachment is preferably implemented by position 5 on cytosine, thymine and uracil, and position N-4 on cytidine.

The use of the term “cleavable linker” does not mean that the entire linker needs to be removed (e.g., from the nucleotide base). When the label is attached to the base, the nucleoside cleavage site can be located at a position on the linker and the position can ensure that a part of the linker remains attached to the nucleotide base after cleavage.

Suitable linkers include, but are not limited to, disulfide linkers, acid-labile linkers (including dialkoxybenzyl linkers, Sieber linkers, indole linkers, tert-butyl Sieber Linkers), electrophilic cleavable linkers, nucleophilic cleavable linkers, photo-cleavable linkers, linkers cleaved under reducing and oxidizing conditions, safety-catch linkers, and linkers that are cleaved through elimination mechanisms. Suitable linkers can be modified with standard chemical protective groups, as disclosed in Greene & Wuts, Protective Groups in Organic Synthesis, John Wiley & Sons. Guillier et al. disclosed other suitable cleavable linkers for solid phase synthesis (Chem. Rev. 100:2092-2157, 2000).

The linkers can be cleaved by any suitable method, including exposure to acids, bases, nucleophiles, electrophiles, free radicals, metals, reducing or oxidizing reagents, light, temperature, enzymes, etc. The suitable cleavage method of various cleavable linkers will be exemplarily described below. Generally, the cleavable linker can be cleaved under the same conditions as the protective group, so that the label and protective group can be removed by only one treatment.

Electrophilic cleavable linkers are typically cleaved by protons and this cleavage includes acid-sensitive cleavage. Suitable electrophilic cleavable linkers include modified benzyl systems, such as trityl, p-alkoxybenzyl ester, and p-alkoxybenzyl amide. Other suitable linkers include tert-butoxycarbonyl (Boc) groups and acetal systems. To prepare suitable linking molecules, it is also taken into consideration the use of thiophilic metals such as nickel, silver or mercury in the cleavage of thioacetals or other sulfur-containing protective groups. Nucleophilic cleavable linkers include groups that are unstable in water (that is, can be simply cleaved at alkaline pH), such as esters, and groups that are unstable to non-aqueous nucleophiles. Fluoride ions can be used to cleave silicon-oxygen bonds in groups such as triisopropylsilane (TIPS) or tert-butyldimethylsilane (TBDMS). Photodegradable linkers are widely used in sugar chemistry. Preferably, the light required to activate cleavage does not affect other components in the modified nucleotide. For example, if a fluorophore is used as a label, it is preferable that the fluorophore absorbs light of a different wavelength from the light required to cleave the linking molecule. Suitable linkers include those linkers based on O-nitrobenzyl compounds and nitroveratryl compounds. Linkers based on benzoin chemistry can also be used (Lee et al., J. Org. Chem. 64:3454-3460, 1999). Various linkers that are sensitive to reductive cleavage are known. Catalytic hydrogenation using palladium-based catalysts has been used to cleave benzyl and benzyloxycarbonyl groups. Disulfide bond reduction is also known in the art. Methods based on oxidation are well known in the art. These methods include the oxidation of alkoxy benzyl and the oxidation of sulfur and selenium linkers. It is also within the scope of the present disclosure to use aqueous iodine to cleave disulfides and other sulfur or selenium-based linkers. Safety-catch linkers are those that are cleaved in two steps. In a preferred system, the first step involves the generation of a reactive nucleophilic center, and the subsequent second step involves intramolecular cyclization, which results in cleavage. For example, the levulinate attachment can be treated with hydrazine or photochemical methods to release an active amine, and then the amine is cyclized to cleave the ester elsewhere in the molecule (Burgess et al., J. Org. Chem.

62:5165-5168, 1997). Elimination reaction can also be used to cleave the linker. Base-catalyzed elimination of groups such as fluorenylmethyloxycarbonyl and cyanoethyl and palladium-catalyzed reduction elimination of allyl systems can be used.

In some embodiments, the linker may include a spacer unit. The length of the linker is not important, as long as the label keeps a sufficient distance from the nucleotide so as not to interfere with the interaction between the nucleotide and the enzyme.

In some embodiments, the linker may consist of a functional group similar to the 3'-OH protective group. In this way, only a single treatment is required to remove the label and the protective group. A particularly preferred linker is an azide-containing linker cleavable by phosphine.

The reagents that can remove the labels from the modified nucleotides as used herein depend to a large extent on the labels used. For example, in the case where a protective group is incorporated into the label, the above-mentioned reagents for removing the protective group are used to remove the label. Alternatively, when the label is attached to the base of the nucleotide through a cleavable linker, the label is removed using the above-mentioned reagents that cleave the linkers. In a preferred embodiment, the same reagent is used to remove the label and the protective group from the modified nucleotide, for example in a case where the linker consists of a functional group similar to the 3'-OH protective group.

Kit

The present disclosure further provides a kit for sequencing a polynucleotide, including:

(a) four nucleotides, wherein the four nucleotides are derivatives of nucleotides A, (T/U), C, and G respectively and have an ability of complementary base pairing; and, a hydroxyl group (—OH) at the 3' site of ribose or deoxyribose of each of the four nucleotides is protected by a protective group; and among the four nucleotides, the first nucleotide is attached to a first molecular label through a cleavable linker 2, the second nucleotide is attached to a first molecular label through a cleavable linker 1, the third nucleotide is attached to a second molecular label through a cleavable linker 1, and the fourth nucleotide is not attached to any molecular label;

(b) two different luciferases, wherein the two luciferases can specifically bind the first molecular label and the second molecular label, respectively; and (c) a cleavage solution for cleaving the linker 2.

In a specific embodiment, the molecular labels used to label the four nucleotides and the labels used to label the two luciferases are as defined above.

In some preferred embodiments, the two different luciferases contained in the kit of the present disclosure contain different labels which can specifically bind the four nucleotides respectively, and the two different luciferases can contain different luciferases, or they can contain different mutants of the same luciferase.

In some preferred embodiments, the kit of the present disclosure further includes: a reagent and/or a device for extracting a nucleic acid molecule from a sample; a reagent for pretreating the nucleic acid molecule; a support to be attached to a to-be-sequenced nucleic acid molecule; a reagent for attaching a to-be-sequenced nucleic acid molecule to a support in, for example, a covalent or non-covalent way; a primer for initiating a nucleotide polymerization reaction; a polymerase for carrying out a nucleotide polymerization reaction; one or more buffer solutions; one or more washing solutions; or any combination thereof.

In some preferred embodiments, the kit of the present disclosure further includes a reagent and/or a device for extracting a nucleic acid molecule from a sample. Methods for extracting a nucleic acid molecule from samples are well known in the art. Therefore, various reagents and/or devices for extracting a nucleic acid molecule, such as reagents for disrupting cells, reagents for precipitating DNA, reagents for washing DNA, reagents for dissolving DNA, reagents for precipitating RNA, reagents for washing RNA, reagents for dissolving RNA, reagents for removing proteins, reagents for removing DNA (for example, when the target nucleic acid molecule is RNA), reagents for removing RNA (for example, when the target nucleic acid molecule is DNA), and any combination thereof can be configured in the kit of the present disclosure as required.

In some preferred embodiments, the kit of the present disclosure further includes a reagent for pretreating a nucleic acid molecule. In the kit of the present disclosure, the reagent used for pretreating the nucleic acid molecule is not subject to additional restrictions, and can be selected according to actual needs. The reagent for pretreating the nucleic acid molecule includes, for example, a reagent (such as DNase I) for fragmentation of the nucleic acid molecule, a reagent (e.g., DNA polymerase, such as T4 DNA polymerase, Pfu DNA polymerase, and Klenow DNA polymerase) for complementing the ends of the nucleic acid molecule, adaptor molecules, label molecules, a reagent (e.g., a ligase, such as T4 DNA ligase) for attaching the adaptor molecule with the target nucleic acid molecule, a reagent (e.g., a DNA polymerase that loses 3'-5' exonuclease activity but shows 5'-3' exonuclease activity) for repairing nucleic acid nicks, a reagent (such as a DNA polymerase, a primer, and a dNTP) for amplifying the nucleic acid molecule, a reagent (such as a chromatography column) for separating and purify the nucleic acid molecule, and any combination thereof.

In some preferred embodiments, the kit of the present disclosure further includes a support to be attached to the to-be-sequenced nucleic acid molecule. The support may have any technical features and any combination of the technical features described in detail above for the support.

For example, in the present disclosure, the support can be made of various suitable materials. Such materials include, for example, inorganic materials, natural polymers, synthetic polymers, and any combination thereof. Specific examples include but are not limited to: cellulose, cellulose derivatives (such as nitrocellulose), acrylic resin, glass, silica gel, polystyrene, gelatin, polyvinylpyrrolidone, copolymers of vinyl and acrylamide, polystyrene crosslinked with divinylbenzene (see, for example, Merrifield Biochemistry 1964, 3, 1385-1390), polyacrylamide, latex, dextran, rubber, silicon, plastic, natural sponge, metal plastic, cross-linked dextran (eg, Sephadex™), Sepharose™, and other supports known to those skilled in the art.

In some preferred embodiments, the support to be attached to the to-be-sequenced nucleic acid molecule may be a solid support including an inert substrate or matrix (such as a glass slide, polymer beads, etc.). The inert substrate or matrix has been functionalized, for example, by applying intermediate materials containing reactive groups that allow the covalent attachment to a biomolecule such as a polynucleotide. Examples of such supports include, but are not limited to, polyacrylamide hydrogels supported on an inert substrate such as glass, particularly the polyacrylamide hydrogels described in WO 2005/065814 and US 2008/0280773, the contents of which are incorporated herein by reference in their entirety. In such embodiments, the biomolecule (e.g., a polynucleotide) can be directly covalently attached to an intermediate material (e.g., hydrogel), and the intermediate material itself can be non-covalently attached to the substrate or matrix (e.g., glass substrate). In some preferred embodiments, the support is a glass slide or silicon wafer modified with a layer of chemical group such as avidin, amino, acrylamide silane or aldehyde group on the surface.

In the present disclosure, the support or solid support is not limited by its size, shape and configuration. In some embodiments, the support or solid support is a planar structure, such as a slide, chip, microchip, and/or array. The surface of such a support may be in the form of a planar layer. In some embodiments, the support or its surface is non-planar, such as an inner or outer surface of a tube or container. In some embodiments, the support or solid support includes microspheres or beads. In certain preferred embodiments, the support to be attached to the to-be-sequenced nucleic acid molecule is an array of beads or wells.

In some preferred embodiments, the kit of the present disclosure further includes a reagent for attaching (e.g., covalently or non-covalently attaching) the to-be-sequenced nucleic acid molecule to the support. Such reagent includes, for example, a reagent for activating or modifying the nucleic acid molecule (such as its 5' end), such as phosphoric acid, thiol, amine, carboxylic acid, or aldehyde; a reagent for activating or modifying the surface of the support, such as amino-alkoxysilane (such as aminopropyltrimethoxysilane, aminopropyltriethoxysilane, 4-aminobutyltriethoxysilane, etc.); a crosslinking agent, such as succinic anhydride, phenyl diisothiocyanate (Guo et al., 1994), maleic anhydride (Yang et al., 1998), 1-ethyl-3-(3-dimethylaminopropyl)-carbodiimide hydrochloride (EDC), meta-maleimidobenzoic acid-N-hydroxysuccinimide ester (MBS), N-succinimidyl [4-iodoacetyl]aminobenzene formic acid (SIAB), 4-(N-maleimidomethyl)cyclohexane-1-carboxylic acid succinimide (SMCC), N-γ-maleimidobutyryloxy-succinimide ester (GMBS), 4-(p-maleimidophenyl) butyric acid succinimide (SMPB); and any combination thereof.

In some preferred embodiments, the kit of the present disclosure further includes a primer for initiating the nucleotide polymerization reaction. In the present disclosure, the primer is not subject to additional restrictions as long as it can specifically anneal to a region of the target nucleic acid molecule. In some exemplary embodiments, the length of the primer may be 5-50 bp, such as 5-10, 10-15, 15-20, 20-25, 25-30, 30-35, 35-40, 40-45, and 45-50 bp. In some exemplary embodiments, the primer may include naturally-occurring or non-naturally-occurring nucleotides. In some exemplary embodiments, the primer contains or consists of naturally-occurring nucleotides. In some exemplary embodiments, the primer includes a modified nucleotide, such as locked nucleic acid (LNA). In some preferred embodiments, the primer contains a universal primer sequence.

In some preferred embodiments, the kit of the present disclosure further includes a polymerase for carrying out a nucleotide polymerization reaction. In the present disclosure, various suitable polymerases can be used. In some exemplary embodiments, the polymerase (e.g., DNA polymerase) can use DNA as a template to synthesize a new DNA strand. In some exemplary embodiments, the polymerase (e.g., reverse transcriptase) can use RNA as a template to synthesize a new DNA strand. In some exemplary embodiments, the polymerase (e.g., RNA polymerase) can use DNA or RNA as a template to synthesize a new RNA strand. Therefore, in some preferred embodiments, the polymerase is selected from DNA polymerase, RNA polymerase, and reverse transcriptase.

In some preferred embodiments, the kit of the present disclosure further includes one or more buffer solutions. Such buffers include, but are not limited to, a buffer solution for DNase I, a buffer solution for DNA polymerase, a buffer solution for ligase, a buffer solution for eluting nucleic acid molecules, a buffer solution for dissolving the nucleic acid molecule, a buffer solution for nucleotide polymerization reaction (e.g., PCR), and a buffer solution for ligation reaction. The kit of the present disclosure may include any one or more of the above-mentioned buffer solutions.

In some preferred embodiments, the kit of the present disclosure further comprises one or more washing solutions. Examples of such washing solutions include, but are not limited to, phosphate buffer, citrate buffer, Tris-HCl buffer, acetate buffer, carbonate buffer, and more. The kit of the present disclosure may include any one or more of the aforementioned washing solutions.

Beneficial Effects of the Disclosure

Compared with the prior art, the technical solution of the present disclosure has the following beneficial effects.

In the method of the present disclosure, molecular labels and nucleotide derivatives are attached through cleavable linkers. Based on a kinetic curve of chemiluminescence reaction, a chemiluminescent label on a specific base is inactivated by a selective chemical bond breaking method, and the secondary luminescence determination is performed by virtue of the luminescence ability of the remaining luminescent label to identify the base. Since only two characteristics of Flash and Glow are required for the kinetic curve of chemiluminescence, the confusion caused by the unobvious characteristics of the kinetic curve can be greatly reduced. In the meanwhile, for the secondary luminescence, only the signal intensity is required to exceed a background value and the characteristics of the kinetic curve are not required, so the adverse effect of side reactions on signal identification during the reaction process can be reduced, and the accuracy of base identification can be improved.

Although the specific embodiments of this disclosure have been described in detail, those skilled in the art will understand that various modifications and changes can be made to the details according to all the teachings that have been disclosed, and these changes are within the protection scope of this disclosure. The full scope of the disclosure is given by the appended claims and any equivalents thereof.

EXAMPLES

Example 1

1. Building of Sequencing Library (1) The following DNA sequence was designed:

GATATCTGCAGGCATAGAATGAATATTATTGAATCAATAATTAAAGTCGGAGGCC
AAGCGGTCTTAGGAAGACAACAACTCCTTGGCTCACAGAACGACATGGCTACGAT
CCGACTT*TACTACTACG*ATAATGGGCTGGATACATGGAATGATTATAGATATATTAAG
GAATAATGTTAATTAATGCCTAAATTAATTAATCTAAGGGGGTTAATACTTCAGCCT
GTGATATC.

For the convenience of library building, oligo sequences (in bold font) were added at both ends of the sequence, and an adaptor sequence of BGISEQ-500 (shaded part) was incorporated in the middle. The bold part in italics was the first 10 bp of the sequence to be determined. The above sequence was synthesized by GenScript Biotech. For unlimited use of the sequence, the synthesized sequence was incorporated into a pUC57 vector and transformed into *E. coli* bacteria.

(2) A suitable amount of *E. coli* bacteria containing a known library were cultivated, and the plasmid was extracted. The following pair of primers were designed: GATATCTGCAGGCAT (SEQ ID NO. 2, primer 1), GATATCACAGGCTGA (SEQ ID NO. 3, primer 2), the known sequence was amplified according to the following system (Table 1) and process (Table 2), and the PCR product was purified with magnetic beads. The purified PCR product was added to split oligo (ATGCCTGCAGATATCGATATCACAGGCTGA, SEQ ID NO. 4) and a cyclization library was built according to the BGISEQ-500 SE50 cyclization library building kit (made by MGI) and process, and the built cyclization library was for later use.

TABLE 1

(Enzymes used were produced by BGI)

| | 1 | x |
|---|---|---|
| 5× High-fidelity enzyme reaction solution | 20 | ul |
| dNTPs mixture (10 mM for each) | 5 | ul |
| High-fidelity enzyme (1 U/ul) | 1 | ul |
| Primer 1 (20 uM) | 6 | ul |
| Primer 2 (20 uM) | 6 | ul |
| Plasmid DNA template (20 ng/ul) | 1 | ul |
| Molecular water | 61 | ul |
| Total volume | 100 | ul |

TABLE 2

| | | |
|---|---|---|
| 98° C. | 3 min; | |
| 98° C. | 20 s | |
| 60° C. | 15 s | 33 Cycles |
| 72° C. | 30 s | |
| 72° C. | 5 min | |
| 4° C. | ∞ | |

2. Amplification of Library Sequence

A Streptavidin-coated 96-well plate was purchased from Thermo Fisher Company; 100 ul of a 1 uM 5' end biotin modified primer GCCATGTCGTTCTGTGAGCCAAGG (SEQ ID NO. 5) was incubated in one of the wells at room temperature for 30 min, the reaction solution was removed; 6 ng of the library built in the above and 20 ul of DNB preparation buffer I in the BGISEQ-500 kit (made by MGI) were added for primer hybridization with the above-mentioned biotin modified primer at 60° C. for 5 min, and then 40 ul of DNB polymerase I and 4 ul of DNB polymerase II in the BGISEQ-500 sequencing kit (MGI) were added to react at 30° C. for 60 min; then, the reaction system was heated to 65° C. to terminate the reaction, and the reaction solution was removed carefully. 100 ul of a 5 uM sequencing primer GCTCACAGAACGACATGGCTACGATCCGACTT (SEQ ID NO. 6) was added to have hybridization reaction at room temperature for 30 min, and then the reaction solution was removed carefully.

3. Sequencing (1) Four dNTPs shown below were synthesized by Acme Bioscience, where Linker 1 was an azide-containing linker, and Linker 2 was a linker containing disulfide bonds:

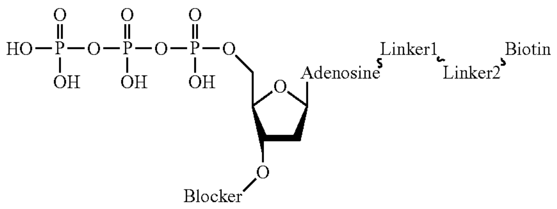

dATP-Linker1-Linker2-biotin

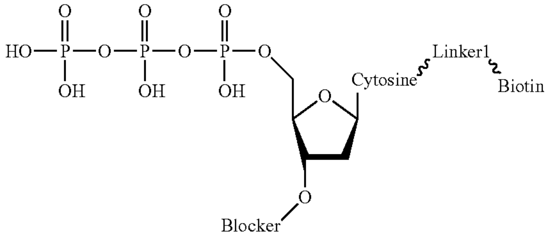

dCTP-Linker1-biotin

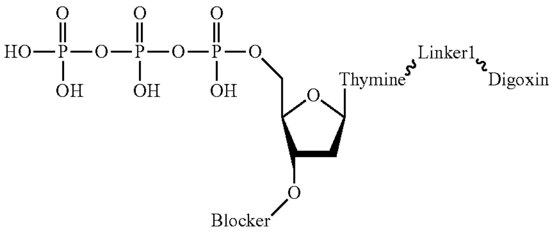

dTTP-Linker1-digoxin

-continued

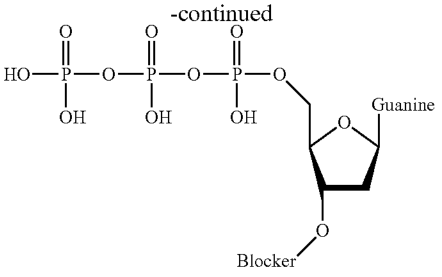

dGTP (2) Preparation of reagents:

The following reagents required in the sequencing reaction were prepared.

Polymerization reaction solution: 50 mM Tris-HCl, 50 mM NaCl, 10 mM $(NH_4)_2SO_4$, 0.02 mg/ml polymerase BG9 (BGI), 3 mM $MgSO_4$, 1 mM EDTA, 1 uM each of the above four dNTPs;

Polymerization buffer: 50 mM Tris-HCl, 50 mM NaCl, 0.05% Tween20;

Elution buffer: 5×SSC, 0.05% Tween20;

Self-luminescence enzyme reaction solution: TBST buffer, 0.5M NaCl, 2 ug/ml SA-NanoKAZ-glow (promega), 2 ug/ml anti-digoxin-Gluc(8990)-flash;

Luminescent substrate solution: a buffer comprising 50 mM Tris-HCl and 0.5 M NaCl was prepared; 50× Coelenterazine (nanolight) and 50× Coelenterazine-f(nanolight) were mixed in a ratio of 1:1 and the mixed solution was then diluted to 2×;

Cleavage buffer: 10 mM DTT, 50 mM Tris-HCl, 50 mM NaCl; the pH was adjusted to 9.0 with 10 M NaOH;

Excision buffer: 20 mM THPP, 0.5 M NaCl, 0.05% tween20;

(3) The sequencing process is shown in FIG. 1.

a. Polymerization: 100 ul of a polymerase reaction solution was added to the well containing the amplified library, the temperature of the microplate reader was increased to 55° C., and reaction lasted for 3 min to polymerize the four dNTPs to the amplified library. The reaction solution was removed carefully, 100 ul of elution reaction solution was then added, the reaction solution was then gently pipetted several times and the elution reaction solution was then removed.

b. Luminescent label binding: 100 ul of self-luminescence enzyme reaction solution 1 was added and incubation was performed at 35° C. for 30 min so that SA-NanoKAZ-glow was bound to dATP-linker1-linker2-biotin and dCTP-linker1-biotin, and anti-digoxin-Gluc(8990)-flash was bound to dTTP-linker1-digoxin. The reaction solution was then removed, and eluent was then added, gently pipetted several times and then removed.

c. Self-luminescence detection 1: the parameters of the microplate reader were set, and the luminescent substrate solution was then added, and self-luminescence curve was then detected; the first signal reading and recording were carried out according to the signal curve graph. 200 ul of eluent was added, the reaction solution was then gently pipetted several times and the eluent was then removed.

d. Chemical bond cleavage: 200 ul of bond cleavage buffer was added to react for 3 min and then the bond cleavage buffer was removed; washing with 200 ul of elution buffer was carried out three times and the eluent was then removed.

e. Self-luminescence detection 2: the parameters of the microplate reader were set, and the luminescent substrate solution was then added, the self-luminescence intensity was then tested, and then the second signal reading and recording were carried out. 200 ul of eluent was added, the reaction solution was then gently pipetted several times and the eluent was then removed.

f. Excision: the self-luminescence reaction solution was removed, and 200 ul of elution buffer was added, gently pipetted several times, and then removed; 100 ul of excision reaction solution was then added to react at 55° C. for 3 min, and the excision reaction solution was then removed; washing with 200 ul of elution buffer was carried out three times.

g. Steps a to f were repeated for the next sequencing cycle.

Figure 2:
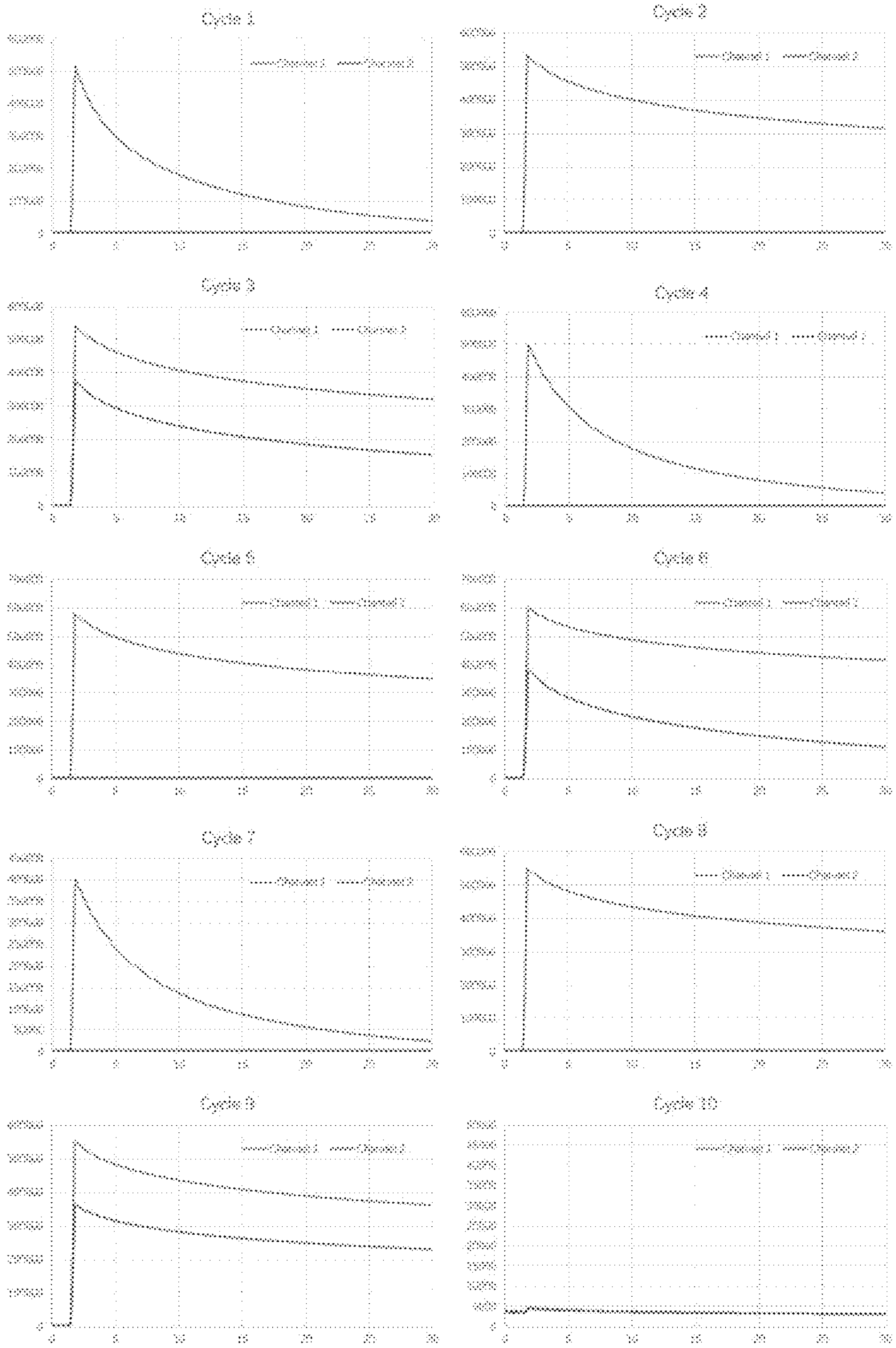
FIG. 2 shows sequencing results of an example of the sequencing method according to the present disclosure, showing a sequencing signal curve of each sequencing cycle.

(4) Sequencing results a. The 10 bp sequencing signal curve is shown in FIG. 2:

b. Analysis of sequencing results:

The signal change curves of all cycles were compared. As shown in the figure, the following can be determined according to the form of signal decline in each cycle:

Nucleotide A: Cycle 2, Cycle 5, Cycle 8;

Nucleotide T: Cycle 1, Cycle 4, Cycle 7;

Nucleotide C: Cycle 3, Cycle 6, Cycle 9;

Nucleotide G: Cycle 10;

Matched with the first 10 bp base sequence of the to-be-sequenced library: TACTACTACG (SEQ ID NO. 7).

Example 2

1. Building of Sequencing Library (1) The following DNA sequence was designed:

GATATCTGCAGGCATAGAATGAATATTATTGAATCAATAATTAAAGTCGGAGGCC

AAGCGGTCTTAGGAAGACAACAACTCCTTGGCTCACAGAACGACATGGCTACGAT

CCGACTT*TACTACTACG*ATAATGGGCTGGATACATGGAATGATTATAGATATATTAAG

GAATAATGTTAATTAATGCCTAAATTAATTAATCTAAGGGGGTTAATACTTCAGCCT

GTGATATC.

For the convenience of library building, oligo sequences (in bold font) were added at both ends of the sequence, and an adaptor sequence of BGISEQ-500 (shaded part) was incorporated in the middle. The bold part in italics was the first 10 bp of the sequence to be determined. The above sequence was synthesized by GenScript Biotech. For unlimited use of the sequence, the synthesized sequence was incorporated into a pUC57 vector and transformed into *E. coli* bacteria.

(2) A suitable amount of *E. coli* bacteria containing a known library were cultivated, and the plasmid was extracted. The following pair of primers were designed: GATATCTGCAGGCAT (SEQ ID NO. 2, primer 1), GATATCACAGGCTGA (SEQ ID NO. 3, primer 2), the known sequence was amplified according to the following system (Table 1) and process (Table 2), and the PCR product was purified with magnetic beads. The purified PCR product was added to split oligo (ATGCCTGCAGATATCGATATCACAGGCTGA SEQ ID NO. 4) and a cyclization library was built according to the BGISEQ-500 SE50 cyclization library building kit (made by MGI) and process, and the built cyclization library was for later use.

TABLE 1

(Enzymes used were produced by BGI)

| | 1 | x |
|---|---|---|
| 5× High-fidelity enzyme reaction solution | 20 | ul |
| dNTPs mixture (10 mM for each) | 5 | ul |
| High-fidelity enzyme (1 U/ul) | 1 | ul |
| Primer 1 (20 uM) | 6 | ul |
| Primer 2 (20 uM) | 6 | ul |
| Plasmid DNA template (20 ng/ul) | 1 | ul |
| Molecular water | 61 | ul |
| Total volume | 100 | ul |

TABLE 2

| | | |
|---|---|---|
| 98° C. | 3 min; | |
| 98° C. | 20 s | |
| 60° C. | 15 s | 33 Cycles |
| 72° C. | 30 s | |
| 72° C. | 5 min | |
| 4° C. | ∞ | |

2. Amplification of Library Sequence

A Streptavidin-coated 96-well plate was purchased from Thermo Fisher Company; 100 ul of a 1 uM 5' end biotin modified primer GCCATGTCGTTCTGTGAGCCAAGG (SEQ ID NO. 5) was incubated in one of the wells at room temperature for 30 min, the reaction solution was removed; 6 ng of the library built in the above and 20 ul of DNB preparation buffer I in the BGISEQ-500 kit (made by MGI) were added for primer hybridization with the above-mentioned biotin modified primer at 60° C. for 5 min, and then 40 ul of DNB polymerase I and 4 ul of DNB polymerase II in the BGISEQ-500 sequencing kit (MGI) were added to react at 30° C. for 60 min; then, the reaction system was heated to 65° C. to terminate the reaction, and the reaction solution was removed carefully. 100 ul of a 5 uM sequencing primer GCTCACAGAACGACATGGCTACGATCCGACTT (SEQ ID NO. 6) was added to have hybridization reaction at room temperature for 30 min, and then the reaction solution was removed carefully.

(1) Four dNTPs shown below were synthesized by Acme Bioscience, where Linker 1 was an azide-containing linker, and Linker 2 was a linker containing cis-aconitic anhydride:

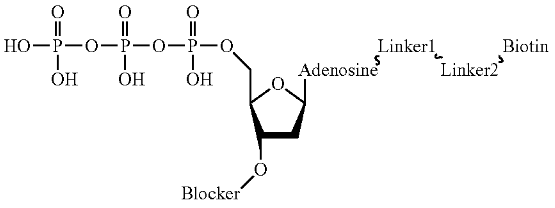

dATP-Linker1-Linker2-biotin

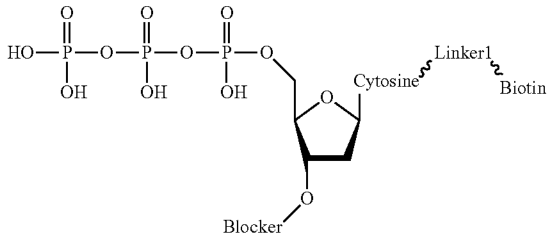

dCTP-Linker1-biotin

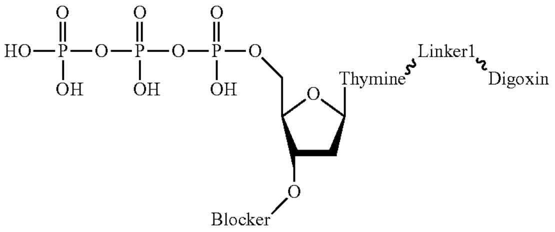

dTTP-Linker1-digoxin

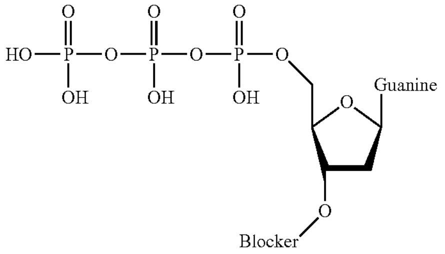

dGTP (2) Preparation of reagents:

The following reagents required in the sequencing reaction were prepared.

Polymerization reaction solution: 50 mM Tris-HCl, 50 mM NaCl, 10 mM $(NH_4)_2SO_4$, 0.02 mg/ml polymerase BG9 (BGI), 3 mM $MgSO_4$, 1 mM EDTA, 1 uM each of the above four dNTPs;

Polymerization buffer: 50 mM Tris-HCl, 50 mM NaCl, 0.05% Tween20;

Elution buffer: 5×SSC, 0.05% Tween20;

Self-luminescence enzyme reaction solution: TBST buffer, 0.5 M NaCl, 2 μg/ml SA-Gluc(M2)-glow (nanolight), 2 μg/ml anti-digoxin-Gluc(8990)-flash;

Luminescent substrate solution: a buffer comprising 50 mM Tris-HCl and 0.5 M NaCl was prepared; 50× Coelenterazine (nanolight) was dissolved in the buffer to 3×;

Cleavage buffer: pH 3.5, 50 mM PBS buffer;

Excision buffer: 20 mM THPP, 0.5 M NaCl, 0.05% tween20;

(3) The sequencing process is shown in FIG. 1.

a. Polymerization: 100 ul of a polymerase reaction solution was added to the well containing the amplified library, the temperature of the microplate reader was increased to 60° C., and reaction lasted for 3 min to polymerize the four dNTPs to the amplified library. The reaction solution was removed carefully, 100 ul of elution reaction solution was then added, the reaction solution was then gently pipetted several times and the elution reaction solution was then removed.

b. Luminescent label binding: 100 ul of self-luminescence enzyme reaction solution 1 was added and incubation was performed at 35° C. for 30 min so that SA-Gluc(M2)-glow was bound to dATP-linker1-linker2-biotin and dCTP-linker1-biotin, and anti-digoxin-Gluc(8990)-flash was bound to dTTP-linker1-digoxin. The reaction solution was then removed, and eluent was then added, gently pipetted several times and then removed.

c. Self-luminescence detection 1: the parameters of the microplate reader were set, and the luminescent substrate solution was then added, and self-luminescence curve was then detected; the first signal reading and recording were carried out according to the signal curve graph. 200 ul of eluent was added, gently pipetted several times and then removed.

d. Chemical bond cleavage: 200 ul of bond cleavage buffer was added to react for 30 min and then the bond cleavage buffer was removed; washing with 200 ul of elution buffer was carried out three times and the eluent was then removed.

e. Self-luminescence detection 2: the parameters of the microplate reader were set, and the luminescent substrate solution was then added, the self-luminescence intensity was then tested, and then the second signal reading and recording were carried out. 200 ul of eluent was added, the reaction solution was then gently pipetted several times and the eluent was then removed.

f. Excision: the self-luminescence reaction solution was removed, and 200 ul of elution buffer was added, gently pipetted several times and then removed; 100 ul of excision reaction solution was then added to react at 60° C. for 3 min, and the excision reaction solution was then removed; washing with 200 ul of elution buffer was carried out three times.

g. Steps a to f were repeated for the next sequencing cycle.

Figure 3:
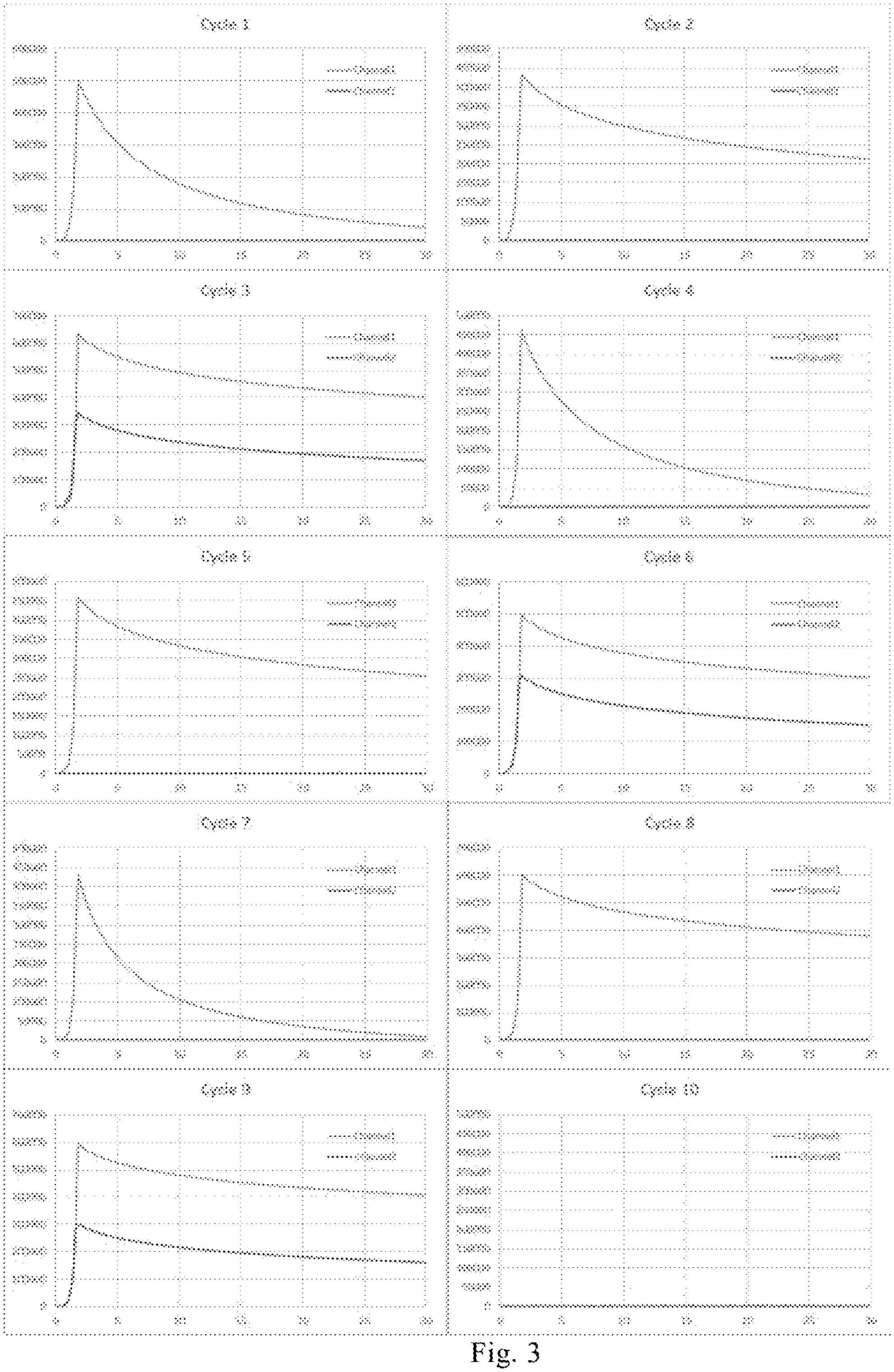
FIG. 3 shows sequencing results of an example of the sequencing method according to the present disclosure, showing a sequencing signal curve of each sequencing cycle.

(4) Sequencing results a. The 10 bp sequencing signal curve is shown in FIG. 3:

b. Analysis of sequencing results:

The signal change curves of all cycles were compared. As shown in the figure, the following can be determined according to the form of signal decline in each cycle:

Nucleotide A: Cycle 2, Cycle 5, Cycle 8;

Nucleotide T: Cycle 1, Cycle 4, Cycle 7;

Nucleotide C: Cycle 3, Cycle 6, Cycle 9;

Nucleotide G: Cycle 10;

Matched with the first 10 bp base sequence of the to-be-sequenced library:

```
                                        (SEQ ID NO. 7)
TACTACTACG.
```

The invention claimed is:

1. A method for sequencing a nucleic acid molecule, comprising:

(a) providing nucleotides A, G, C, and (T/U), wherein three of the nucleotides are respectively attached to chemiluminescent labels by linkers, wherein before and after cleavage of the linkers, the chemiluminescent label attached to each nucleotide shows a different luminescence kinetics or luminescence form different from that of the chemiluminescent labels attached to other nucleotides; wherein the first nucleotide is attached to the first molecular label through linker 1-linker 2; the second nucleotide is attached to the first molecular label through linker 1; the third nucleotide is attached to the second molecular label through linker 1; the fourth nucleotide is not attached to any molecular label;

(b) incorporating a nucleotide into a complementary strand of the nucleic acid;

(c) detecting the chemiluminescent label of the nucleotide of step (b);

(d) removing the linker of the nucleotide of step (b);

(e) detecting the chemiluminescent label of the nucleotide of step (b) after the treatment in step (d) to determine a type of the nucleotide incorporated;

(f) optionally, removing the chemiluminescent label of the nucleotide of step (b); and (g) optionally, repeating steps (b) to (f) or steps (b) to (e) one or more times to sequence a target single-stranded polynucleotide;

wherein detecting the chemiluminescent label of the nucleotide of step (b) comprises: making the chemiluminescent label to come into contact with a suitable substrate to trigger a chemiluminescence reaction, and detecting luminescence kinetics of light emitted therefrom; the chemiluminescent label is selected from biochemiluminescent labels that induce different luminescence kinetics and any combination thereof; or detecting the chemiluminescent label of the nucleotide of step (b) comprises: making the chemiluminescent label to come into contact with a suitable substrate to trigger the chemiluminescence reaction, and detecting a luminescence form of light emitted therefrom; the chemiluminescent label is selected from biochemiluminescent labels that induce different luminescence forms and any combination thereof;

wherein the luminescence forms include flash and glow.

2. The method according to claim 1, wherein a ribose or deoxyribose moiety of each nucleotide contains a protective group attached via a 2' or 3' oxygen atom, and the protective group is modified or removed after the incorporation of the nucleotide so as to expose a 3'-OH group.

3. The method according to claim 1, wherein the chemiluminescent label is attached to the nucleotide by affinity interaction.

4. The method according to claim 1, wherein all the nucleotides are allowed to come into contact with the target single-stranded polynucleotide in sequence, unincorporated nucleotides are removed before the next nucleotide is added, and the detection and removal of the chemiluminescent label are performed after the addition of each nucleotide or the addition of all the four nucleotides.

5. The method according to claim 4, wherein one, two, three or all of the four nucleotides are allowed to come into contact with the target single-stranded polynucleotide at the same time, unincorporated nucleotides are removed before detection, and the detection and removal of the chemiluminescent label are performed after the addition of the one, two, three or all of the four nucleotides.

6. The method according to claim 1, wherein the chemiluminescent label is selected from luciferases that induce different luminescence kinetics and any combination thereof, or the chemiluminescent label is selected from luciferases that induce different luminescence forms and any combination thereof.

7. The method according to claim 1, wherein the chemiluminescent label is a combination of two luciferases that induce different luminescence kinetics, or the chemiluminescent label is a combination of two luciferases that induce different luminescence forms.

8. The method according to claim 2, wherein the chemiluminescent label and the protective group are removed under the same condition.

9. The method according to claim 3, wherein the affinity interaction comprises antigen-antibody interaction or biotin-avidin interaction.

10. The method according to claim 9, wherein the avidin is streptavidin.

11. The method according to claim 3, wherein by attaching the chemiluminescent label to one of members participating in the affinity interaction and attaching the nucleotide to the other member participating in the affinity interaction, the chemiluminescent label is attached to the nucleotide through the affinity interaction between the members.

12. The method according to claim 11, wherein the member attached to the nucleotide is a biotin and the member attached to the chemiluminescent label is an avidin; or the member attached to the nucleotide is digoxin and the member attached to the chemiluminescent label is an anti-digoxin antibody; or the member attached to the nucleotide is digoxin and the member attached to the chemiluminescent label is an avidin, wherein the digoxin and the avidin are bound by affinity with an anti-digoxin antibody attached to the biotin.

13. The method according to claim 12, wherein the avidin is streptavidin.

* * * * *